United States Patent
Al-Omair et al.

(10) Patent No.: US 11,857,972 B1
(45) Date of Patent: Jan. 2, 2024

(54) CORE SAMPLE HOLDER FOR MICROWAVE HEATING OF A CORE SAMPLE

(71) Applicant: KUWAIT UNIVERSITY, Safat (KW)

(72) Inventors: Osamah Al-Omair, Safat (KW); Nyeso Christian Azubuike, Safat (KW); Ahmad Essam Abdel Halim Omar, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 17/847,144

(22) Filed: Jun. 22, 2022

(51) Int. Cl.
| | |
|---|---|
| *B01L 7/00* | (2006.01) |
| *G01N 33/24* | (2006.01) |
| *G01N 15/08* | (2006.01) |
| *E21B 49/00* | (2006.01) |
| *G01N 35/00* | (2006.01) |

(52) U.S. Cl.
CPC ............... *B01L 7/00* (2013.01); *E21B 49/00* (2013.01); *G01N 15/082* (2013.01); *G01N 15/0806* (2013.01); *G01N 33/24* (2013.01); *B01L 2300/1866* (2013.01); *G01N 2035/00405* (2013.01); *G01N 2203/0019* (2013.01); *G01N 2203/0256* (2013.01); *G01N 2203/0266* (2013.01)

(58) Field of Classification Search
CPC .... B01L 7/00; B01L 2300/1866; E21B 49/00; G01N 15/0806; G01N 15/082; G01N 33/24; G01N 2035/00405; G01N 2203/0019; G01N 2203/0256; G01N 2203/0266

See application file for complete search history.

(56) References Cited

U.S. PATENT DOCUMENTS

| | | | |
|---|---|---|---|
| 4,599,891 A | 7/1986 | Brauer et al. | |
| 4,710,948 A | 12/1987 | Withjack | |
| 4,827,761 A | * 5/1989 | Vinegar | ............... G01R 33/307 378/208 |
| 4,996,872 A | 3/1991 | Mueller et al. | |

(Continued)

FOREIGN PATENT DOCUMENTS

| | | | |
|---|---|---|---|
| CN | 104267174 A | | 1/2015 |
| CN | 107817202 A | * | 3/2018 |

(Continued)

*Primary Examiner* — Ryan D Walsh
(74) *Attorney, Agent, or Firm* — Nath, Goldberg & Meyer; Richard C. Litman

(57) ABSTRACT

The core sample holder for microwave heating of a core sample includes a hollow housing having opposed open first and second ends. A resilient sleeve is disposed within the hollow housing. An annular bladder is disposed within the hollow housing and surrounds the resilient sleeve. The annular bladder is adapted for receiving a liquid. An annular cavity is defined between the outer surface of the annular bladder and the inner surface of the hollow housing and is adapted for receiving a pressurized fluid through at least one pressurized fluid port. First and second caps releasably cover and seal the first and second ends of the hollow housing, respectively. A microwave waveguide passes through the wall of the hollow housing and the annular cavity for transmitting microwave radiation from an external microwave source into the liquid contained within the annular bladder to heat the liquid.

15 Claims, 2 Drawing Sheets

(56) References Cited

U.S. PATENT DOCUMENTS

| | | | | |
|---|---|---|---|---|
| 5,065,421 | A * | 11/1991 | Morineau | G01N 33/241 |
| | | | | 378/208 |
| 5,253,518 | A * | 10/1993 | Steiger | G01N 33/241 |
| | | | | 166/250.01 |
| 5,263,360 | A * | 11/1993 | Blauch | C09K 8/94 |
| | | | | 73/38 |
| 5,382,414 | A * | 1/1995 | Lautenschlager | B01J 19/126 |
| | | | | 422/186 |
| 6,803,237 | B2 | 10/2004 | Manganini et al. | |
| 7,861,609 | B2 * | 1/2011 | Haggerty | G01N 33/24 |
| | | | | 73/866.5 |
| 8,356,510 | B2 | 1/2013 | Coenen | |
| 9,687,851 | B2 | 6/2017 | Feilders et al. | |
| 10,844,711 | B2 * | 11/2020 | Cooper | E21B 49/02 |
| 11,054,351 | B2 * | 7/2021 | Li | G01D 21/02 |
| 2013/0326900 | A1 * | 12/2013 | James | F26B 3/30 |
| | | | | 34/245 |
| 2015/0268314 | A1 | 9/2015 | Peterson | |

FOREIGN PATENT DOCUMENTS

| | | | | | |
|---|---|---|---|---|---|
| CN | 113075112 | A | * | 7/2021 | |
| DE | 3627966 | A1 | | 8/1987 | |
| EP | 1935485 | A1 | * | 6/2008 | B01J 19/0053 |

\* cited by examiner

CORE SAMPLE HOLDER FOR MICROWAVE HEATING OF A CORE SAMPLE

BACKGROUND

1. Field

The disclosure of the present patent application relates to measurement and testing of reservoir rock core samples, and particularly to a core sample holder for microwave heating of a core sample during testing.

2. Description of the Related Art

The extraction and analysis of reservoir rock samples is a common practice in the oil industry. Conventionally, reservoir core samples are extracted and then cut into cylindrical shapes having fixed diameters and flat ends. During laboratory testing, the reservoir core samples are typically subjected to high pressures and temperatures in order to simulate the conditions of their native underground environments. However, as well depths increase, the corresponding down-hole pressures and temperatures also increase. Thus, laboratory testing equipment requires constant upgrading in order to simulate these ever-increasing pressures and temperatures.

For conducting these simulations, special core holders are used for analyzing the cylindrical core samples. In use, reservoir fluids are injected into the core sample through one end of the holder and discharged through the opposite end. This allows for study of fluid migration and fluid-rock interactions. In order to simulate the environmental pressure conditions, a secondary fluid source is used to provide confinement pressure outside the rock at the corresponding down-hole temperature.

In a typical core holder, the heat for raising the temperature is typically supplied by an external jacket, or alternatively, the entire sample holder is placed inside an oven. In either case, heat is transferred from the exterior via conduction, first through the thick housing of the sample holder and then through the sleeve holding the core sample. This method of heat transfer is extremely time consuming and often inefficient, particularly when very high temperatures are required. Thus, a core sample holder for microwave heating of a core sample solving the aforementioned problems is desired.

SUMMARY

The core sample holder for microwave heating of a core sample uses microwave-based heating of a reservoir rock core sample or the like during testing. The core sample holder for microwave heating of a core sample includes a hollow housing having opposed open first and second ends. At least one pressurized fluid port is formed through a wall of the hollow housing. A resilient sleeve is disposed within the hollow housing. The resilient sleeve is adapted for releasably holding the core sample during testing. The hollow housing may be, for example, a cylindrical housing, and the resilient sleeve may be elongated and axially aligned with an axis of the cylindrical housing.

An annular bladder is also received within the hollow housing and surrounds the resilient sleeve. The annular bladder is adapted for holding a liquid. The liquid may be water, although it should be understood that any suitable liquid that can be heated by applied microwave radiation may be used. The annular bladder may completely cover the outer surface of the resilient sleeve to provide full and even heating of the resilient sleeve and the core sample disposed therein. An annular cavity is defined between the outer surface of the annular bladder and the inner surface of the hollow housing. The annular cavity is adapted for receiving a pressurized fluid, such as pressurized air or the like, through the at least one pressurized fluid port.

First and second caps releasably cover and seal the first and second ends of the hollow housing, respectively. An inlet channel is formed through the first cap for injecting a testing fluid into the core sample, and an outlet channel is formed through the second cap for discharging the testing fluid from the core sample. Each of the first and second caps may have an interior portion having a reduced diameter, such that each of the interior portions releasably covers and seals a corresponding open end of the resilient sleeve. First and second sand screens may be secured to the interior portions of the first and second caps, respectively, such that, in use, the first and second sand screens contact opposed ends of the core sample during testing. The first and second sand screens restrict migration of fine particles from the core sample during testing.

A microwave waveguide passes through the wall of the hollow housing and the annular cavity, such that the microwave waveguide terminates within the annular bladder. The microwave waveguide is adapted for transmitting microwave radiation from an external microwave source into the liquid contained within the annular bladder to heat the liquid.

A temperature sensor, such as a thermocouple or the like, may be embedded in the first cap for monitoring the temperature during testing. A pressure sensor may be coupled with at least one pressurized fluid port for monitoring the pressurized fluid within the annular cavity.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
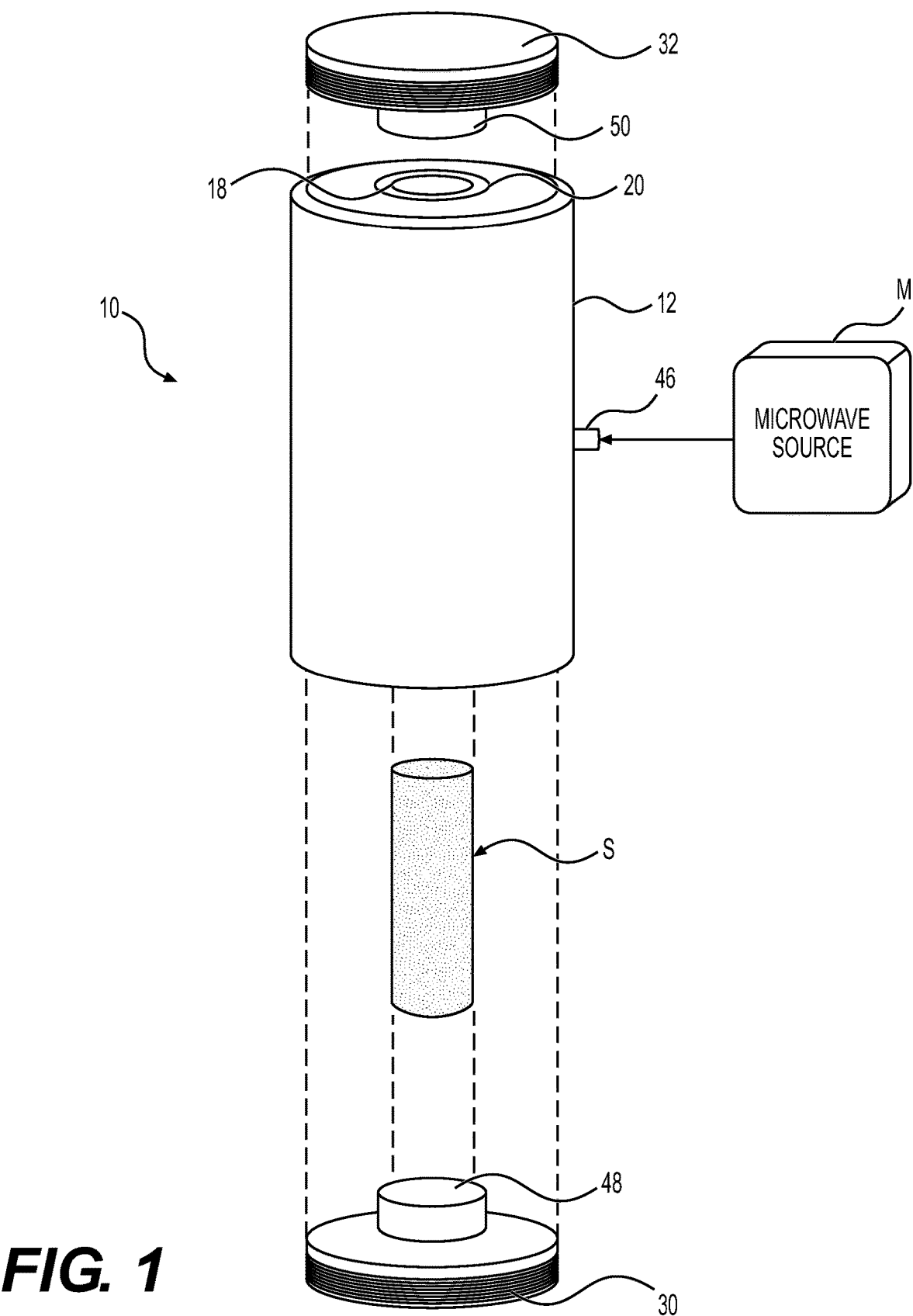
FIG. 1 is a partially exploded perspective view of a core sample holder for microwave heating of a core sample.
Figure 2:
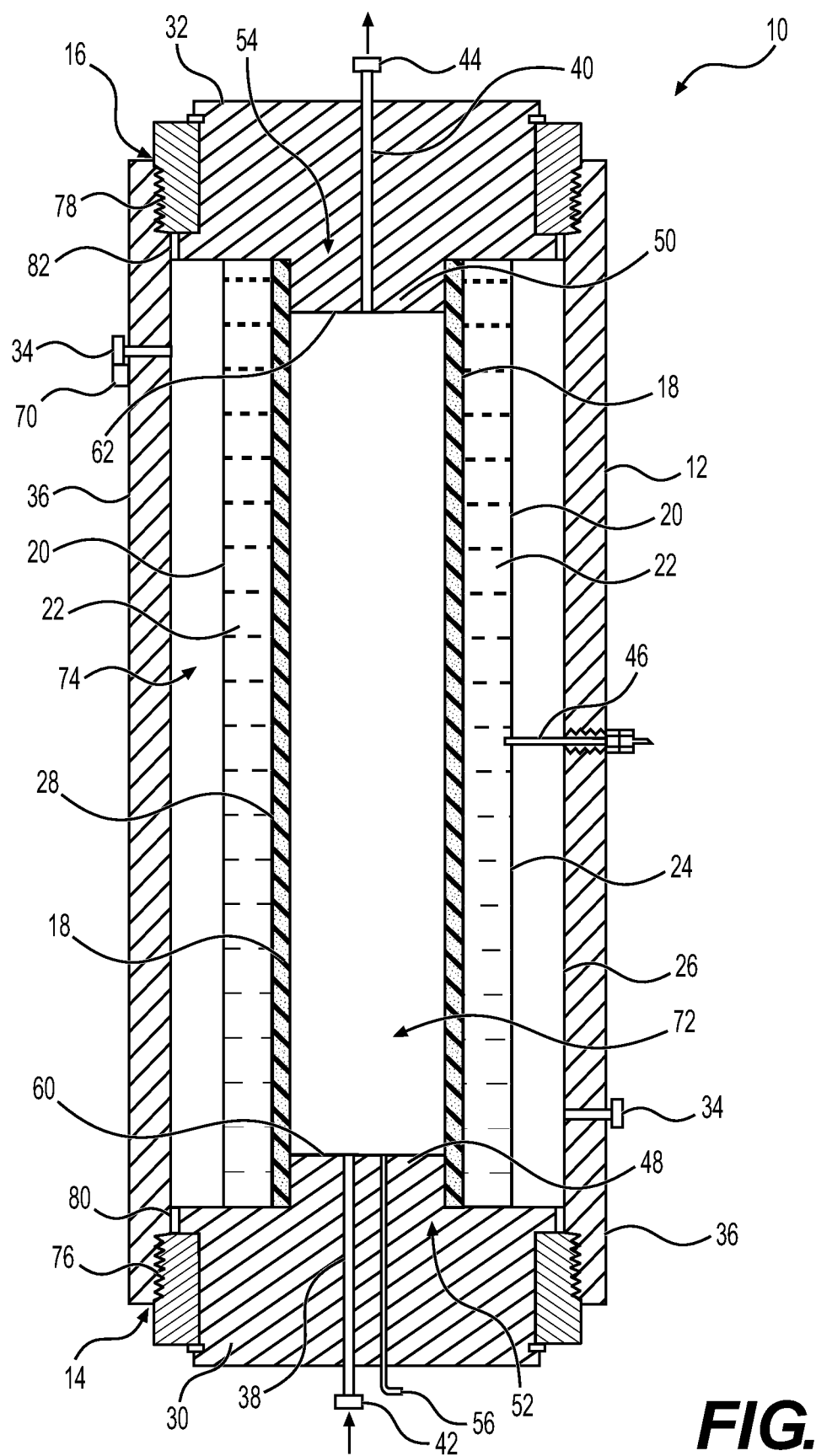
FIG. 2 is side view in section of the core sample holder of FIG. 1.

Referring to FIGS. 1 and 2, the core sample holder for microwave heating of a core sample, designated generally as 10 in the drawings, uses microwave-based heating of a reservoir rock core sample S or the like during testing. The core sample holder 10 includes a hollow housing 12 having opposed open first and second ends 14, 16, respectively, having at least one pressurized fluid port 34 formed through a wall 36 of the hollow housing 12. In FIG. 2, two such pressurized fluid ports 34 are shown. However, it should be understood that any suitable number of pressurized fluid ports 34 may be utilized. It should be further understood that the hollow housing 12 may be formed from any suitable material that can withstand the hydrostatic confining pressure required therein during testing of core sample S. For example, the hollow housing 12 may be formed from a carbon fiber composite material with an aluminum liner.

Alternatively, the hollow housing 12 may be formed from steel, a nickel-chromium-molybdenum-tungsten alloy, or a ceramic zirconia material.

A resilient sleeve 18 is disposed within the hollow housing 12. The resilient sleeve 18 is adapted for releasably holding the core sample S during testing. The hollow housing 12 may be a cylindrical housing, and the resilient sleeve 18 may be elongated and axially aligned with an axis of the cylindrical housing 12. However, it should be understood that the overall shape and relative dimensions of the hollow housing 12 and the resilient sleeve 18 are shown in FIGS. 1 and 2 for exemplary purposes only, and may be varied dependent upon the size, shape and type of samples being tested. It should be further understood that resilient sleeve 18 may be formed from any suitable type of resilient material. For example, resilient sleeve 18 may be formed from neoprene with an internal Teflon® (polytetrafluoroethylene, or PTFE) lining. The resilient sleeve 18 is adapted for securely and releasably retaining the core sample S within an interior region 72 of the sleeve 18.

An annular bladder 20 is also disposed within the hollow housing 12 and surrounds the resilient sleeve 18. The annular bladder 20 is adapted for receiving a liquid 22. The liquid 22 may be water, for example, although it should be understood that any suitable liquid that can be heated by applied microwave radiation may be used. The annular bladder 20 may completely cover an outer surface 28 of the resilient sleeve 18 to provide full and even heating of the resilient sleeve 18 and the core sample S disposed therein. The annular bladder 18 may be formed from silicone rubber, for example, which has a melting temperature ranging between from 200° C. and 450° C. However, it should be understood that the annular bladder 20 may be formed from any suitable material that will not melt or degrade at or near the boiling point of the liquid 22 within the bladder 20.

An annular cavity 74 is defined between an outer surface 24 of the annular bladder 20 and an inner surface 26 of the hollow housing 12. The annular cavity 74 is adapted for receiving a pressurized fluid, such as pressurized air or the like, through the at least one pressurized fluid port 34. During testing, the pressurized fluid within the annular cavity 74 simulates the native pressure within the rock at the depth from which the core sample S was extracted. A pressure sensor 70 may be coupled to one of the pressurized fluid ports 34 for monitoring the pressurized fluid within the annular cavity 74.

First and second caps 30, 32, respectively, releasably cover and seal the first and second ends 14, 16 of the hollow housing 12, respectively. An inlet channel 38 is formed through the first cap 30 for injecting a testing fluid into the core sample S, and an outlet channel 40 is formed through the second cap 32 for discharging the testing fluid from the core sample S. In FIG. 2, exemplary inlet and outlet ports 42, 44 are shown connected to inlet channel 38 and outlet channel 40, respectively, although it should be understood that any suitable type of fluid connection may be used.

As shown, each of the first and second caps 30, 32 may have an interior portion 48, 50, respectively, having a reduced diameter. This allows each of the interior portions 48, 50 to releasably cover and seal the corresponding open end 52, 54 of the resilient sleeve 18, as shown in FIG. 2. First and second sand screens 60, 62 may be attached to the interior portions 48, 50 of the first and second caps 30, 32, respectively, such that, in use, the first and second sand screens 60, 62 contact opposed ends of the core sample S during testing. The first and second sand screens 60, 62 restrict migration of fine particles from the core sample S during testing.

In FIG. 2, the first cap 30 has external threads 76 for engaging corresponding internal threads formed about the open end 14 of the hollow housing 12. Similarly, the second cap 32 has external threads 78 for engaging corresponding internal threads formed about the open end 16 of the hollow housing 12. It should be understood that the threads 76, 78 are shown for exemplary purposes only, and that any suitable type of fastener or engagement may be used to effect releasable covering and sealing of the open ends 14, 16 by the first and second caps 30, 32, respectively. Additional seals, such as O-rings 80, 82, or the like, may also be used to effect a tight and fluid-proof seal.

A microwave waveguide 46 passes through the wall 36 of the hollow housing 12 and the annular cavity 74, such that the microwave waveguide 46 terminates within the annular bladder 20. The microwave waveguide 46 is adapted for transmitting microwave radiation from an external microwave source M into the liquid 22 contained within the annular bladder 20 to heat the liquid. It should be understood that any suitable type of source of microwave radiation may be used, such as a magnetron or the like.

A temperature sensor 56, such as a thermocouple or the like, may be embedded in the first cap 30 for monitoring the temperature during testing. During testing, the liquid 22 is heated to a temperature that simulates the native temperature within the rock at the depth from which the core sample S was extracted. In use, the microwave radiation heats the liquid 22, and the heat is transferred by conduction through the wall of the annular bladder 20 to the resilient sleeve 18, and from the resilient sleeve 18 into the core sample S.

It is to be understood that the core sample holder for microwave heating of a core sample is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A core sample holder for microwave heating of a core sample, comprising:
  a hollow housing having a wall, the housing having opposed open first and second ends and at least one pressurized fluid port forming a passage through the wall of the hollow housing;
  a resilient sleeve disposed within the hollow housing, the resilient sleeve being adapted for releasably holding a core sample;
  an annular bladder disposed within the hollow housing and surrounding the resilient sleeve, the annular bladder being adapted for receiving a liquid, the annular bladder and the hollow housing defining an annular cavity therebetween, the annular cavity being adapted for receiving a pressurized fluid through the at least one pressurized fluid port;
  first and second caps releasably covering and sealing the first and second ends of the hollow housing, respectively, the first cap having an inlet channel defined therein for injecting a testing fluid into the core sample, the second cap having an outlet channel defined therein for discharging the testing fluid from the core sample; and a microwave waveguide passing through the wall of the hollow housing and the annular cavity, such that the microwave waveguide terminates within the annular bladder, the microwave waveguide being adapted for transmitting microwave radiation from an external microwave source into the liquid contained within the annular bladder to heat the liquid.

2. The core sample holder as recited in claim 1, wherein the hollow housing comprises a cylindrical housing.

3. The core sample holder as recited in claim 2, wherein the resilient sleeve is elongated and is axially aligned with the cylindrical housing.

4. The core sample holder as recited in claim 3, wherein the annular bladder completely covers the resilient sleeve.

5. The core sample holder as recited in claim 1, wherein each of the first and second caps has an interior portion having a reduced diameter, each of the interior portions releasably covering and sealing a corresponding open end of the resilient sleeve.

6. The core sample holder as recited in claim 5, further comprising first and second sand screens respectively attached to the interior portions of the first and second caps.

7. The core sample holder as recited in claim 1, further comprising a pressure sensor attached to the at least one pressurized fluid port for monitoring pressure of pressurized fluid within the annular cavity.

8. A core sample holder for microwave heating of a core sample, comprising:
- a hollow housing having a wall defining opposed open first and second ends and having at least one pressurized fluid port forming a passage through the wall of the hollow housing;
- a resilient sleeve disposed within the hollow housing, the resilient sleeve being adapted for releasably holding a core sample;
- an annular bladder disposed within the hollow housing and surrounding the resilient sleeve, the annular bladder being adapted for receiving a liquid, the annular bladder and the hollow housing defining an annular cavity therebetween, the annular cavity being adapted for receiving a pressurized fluid through the at least one pressurized fluid port;
- first and second caps releasably covering and sealing the first and second ends of the hollow housing, respectively, the first cap having an inlet channel defined therein for injecting a testing fluid into the core sample, the second cap having an outlet channel defined therein for discharging the testing fluid from the core sample;
- a temperature sensor embedded in the first cap; and
- a microwave waveguide passing through the wall of the hollow housing and the annular cavity, such that the microwave waveguide terminates within the annular bladder, the microwave waveguide being adapted for transmitting microwave radiation from an external microwave source into the liquid contained within the annular bladder to heat the liquid.

9. The core sample holder as recited in claim 8, wherein the hollow housing comprises a cylindrical housing.

10. The core sample holder as recited in claim 9, wherein the resilient sleeve is elongated and is axially aligned with the cylindrical housing.

11. The core sample holder as recited in claim 10, wherein the annular bladder completely covers the resilient sleeve.

12. The core sample holder as recited in claim 8, wherein the first and second caps each has an interior portion having a reduced diameter, each of the interior portions releasably covering and sealing a corresponding open end of the resilient sleeve.

13. The core sample holder as recited in claim 12, further comprising first and second sand screens attached to the interior portions of the first and second caps, respectively.

14. The core sample holder as recited in claim 8, wherein the temperature sensor comprises a thermocouple.

15. The core sample holder as recited in claim 8, further comprising a pressure sensor attached to the at least one pressurized fluid port for monitoring pressure of the pressurized fluid within the annular cavity.

\* \* \* \* \*